(12) United States Patent
Rodriguez

(10) Patent No.: US 8,875,591 B1
(45) Date of Patent: Nov. 4, 2014

(54) METHODS FOR MEASURING AT LEAST ONE RHEOLOGICAL PROPERTY OF DIAMOND PARTICLES

(75) Inventor: Amy Leigh Rodriguez, South Jordan, UT (US)

(73) Assignee: US Synthetic Corporation, Orem, UT (US)

( * ) Notice: Subject to any disclaimer, the term of this patent is extended or adjusted under 35 U.S.C. 154(b) by 513 days.

(21) Appl. No.: 13/014,777

(22) Filed: Jan. 27, 2011

(51) Int. Cl.
- *G01N 11/02* (2006.01)
- *G01N 11/14* (2006.01)
- *G01N 11/04* (2006.01)

(52) U.S. Cl.
CPC ............... *G01N 11/14* (2013.01); *G01N 11/04* (2013.01)
USPC ............................................. 73/866; 73/818

(58) Field of Classification Search
CPC ........ G01N 11/14; G01N 11/04; G01N 11/10
USPC .................................... 73/818, 841, 847, 866
See application file for complete search history.

(56) References Cited

U.S. PATENT DOCUMENTS

| 4,172,667 | A | * | 10/1979 | Zenz et al. ..................... 366/107 |
| 4,181,023 | A | * | 1/1980 | Clamroth et al. ............... 73/866 |
| 4,268,276 | A | | 5/1981 | Bovenkerk |
| 4,274,286 | A | * | 6/1981 | Gioia .............................. 73/866 |
| 4,410,054 | A | | 10/1983 | Nagel et al. |
| 4,468,138 | A | | 8/1984 | Nagel |
| 4,560,014 | A | | 12/1985 | Geczy |
| 4,633,712 | A | * | 1/1987 | Scieszka ......................... 73/866 |
| 4,719,809 | A | * | 1/1988 | Johanson et al. ............... 73/866 |
| 4,738,322 | A | * | 4/1988 | Hall et al. |
| 4,766,761 | A | * | 8/1988 | Lee .................................. 73/38 |
| 4,811,801 | A | | 3/1989 | Salesky et al. |
| 4,913,247 | A | | 4/1990 | Jones |
| 5,016,718 | A | | 5/1991 | Tandberg |
| 5,092,687 | A | | 3/1992 | Hall |
| 5,109,717 | A | * | 5/1992 | Galetto et al. .................. 73/866 |
| 5,120,327 | A | | 6/1992 | Dennis |
| 5,135,061 | A | | 8/1992 | Newton, Jr. |
| 5,154,245 | A | | 10/1992 | Waldenstrom et al. |
| 5,165,291 | A | * | 11/1992 | Galetto et al. .................. 73/866 |
| 5,364,192 | A | | 11/1994 | Damm et al. |

(Continued)

FOREIGN PATENT DOCUMENTS

WO    WO 2009147629 A1 * 12/2009 ................. B01J 3/06

OTHER PUBLICATIONS

"Brookfield Powder Flow Tester Operating Instructions Manual M09-1200", Brookfield Engineering Laboratories, Inc., 2009.*

(Continued)

*Primary Examiner* — David A Rogers
(74) *Attorney, Agent, or Firm* — Dorsey & Whitney LLP

(57) ABSTRACT

Methods of measuring at least one rheological property of diamond particles used in the manufacture of polycrystalline diamond are disclosed. Diamond particles are provided including a plurality of unsintered diamond particles. A rheological property (e.g., a torsional mechanical property or other flow property) of the diamond particles is measured. By comparing the measured value of the torsional mechanical property to that of a baseline known to correlate to the desired target specification, it may be determined whether the diamond particles are within an acceptable range relative to the target specification. Such a method may be incorporated into methods for manufacturing a polycrystalline diamond compact to ensure the quality of a polycrystalline diamond table thereof.

20 Claims, 8 Drawing Sheets

(56) References Cited

U.S. PATENT DOCUMENTS

| | | | |
|---|---|---|---|
| 5,368,398 A | 11/1994 | Damm et al. | |
| 5,460,233 A | 10/1995 | Meany et al. | |
| 5,467,659 A * | 11/1995 | Young | 73/866 |
| 5,480,233 A | 1/1996 | Cunningham | |
| 5,544,713 A | 8/1996 | Dennis | |
| 5,610,325 A * | 3/1997 | Rajagopal et al. | 73/54.39 |
| 5,847,294 A * | 12/1998 | Poole | 73/866 |
| 6,065,330 A * | 5/2000 | Freeman et al. | 73/54.28 |
| 6,158,293 A * | 12/2000 | Poole | 73/866 |
| 6,481,267 B1 * | 11/2002 | Iles et al. | 73/54.28 |
| 6,782,735 B2 * | 8/2004 | Walters et al. | 73/54.28 |
| 6,793,681 B1 | 9/2004 | Pope et al. | |
| 7,201,040 B2 * | 4/2007 | Bateson et al. | 73/54.28 |
| 7,615,098 B2 * | 11/2009 | Brent et al. | 75/443 |
| 7,784,370 B2 * | 8/2010 | Matsusaka et al. | 73/866 |
| 8,057,775 B2 * | 11/2011 | Vail et al. | 423/446 |
| 8,206,474 B2 * | 6/2012 | Tank et al. | 51/307 |
| 8,216,677 B2 * | 7/2012 | Mukhopadhyay et al. | 428/408 |
| 8,292,006 B2 * | 10/2012 | Scott et al. | 175/434 |
| 8,313,229 B2 * | 11/2012 | Brannon et al. | 366/142 |
| 8,335,343 B2 * | 12/2012 | Martiska et al. | 382/100 |
| 8,361,429 B2 * | 1/2013 | Vail et al. | 423/446 |
| 8,440,303 B2 * | 5/2013 | Mukhopadhyay et al. | 428/408 |
| 2008/0023231 A1 * | 1/2008 | Vail | 175/434 |
| 2011/0072730 A1 * | 3/2011 | Sithebe | 51/297 |
| 2011/0252711 A1 * | 10/2011 | Chakraborty et al. | 51/298 |
| 2012/0118072 A1 * | 5/2012 | Martiska et al. | 73/821 |
| 2012/0260723 A1 * | 10/2012 | Brookfield | 73/54.01 |

OTHER PUBLICATIONS

"FT4 Powder Rheometer System", Freeman Technology, available on the Internet Archive at <http://www.archive.org>, archived on Jan. 3, 2010.*

Brookfield PFT Powder Flow Tester Brochure.

* cited by examiner

METHODS FOR MEASURING AT LEAST ONE RHEOLOGICAL PROPERTY OF DIAMOND PARTICLES

BACKGROUND

Wear-resistant, polycrystalline diamond compacts ("PDCs") are employed in a variety of mechanical applications. For example, PDCs are used in drilling tools (e.g., cutting elements, gage trimmers, etc.), machining equipment, bearing apparatuses, wire-drawing machinery, and in other mechanical apparatuses.

PDCs have found particular utility as superabrasive cutting elements in rotary drill bits, such as roller-cone drill bits and fixed-cutter drill bits. A PDC cutting element typically includes a superabrasive diamond layer commonly known as a polycrystalline diamond ("PCD") table. The diamond table is formed and bonded to a cemented carbide substrate using a high-pressure/high-temperature ("HPHT") process. The PDC cutting element may be brazed directly into a preformed pocket, socket, or other receptacle formed in a bit body. The cemented carbide substrate may often be brazed or otherwise joined to an attachment member, such as a cylindrical backing. A rotary drill bit typically includes a number of PDC cutting elements affixed to the bit body. It is also known that a stud carrying the PDC may be used as a PDC cutting element when mounted to a bit body of a rotary drill bit by press-fitting, brazing, or otherwise securing the stud into a receptacle formed in the bit body.

Conventional PDCs are normally fabricated by placing a cemented tungsten carbide substrate into a container with a volume of diamond particles positioned on a surface of the cemented tungsten carbide substrate. A number of such containers may be loaded into an HPHT press. The substrate(s) and volume(s) of diamond particles are then processed under diamond-stable HPHT conditions. During the HPHT process, a metal-solvent catalyst cementing constituent of the cemented tungsten carbide substrate, such as cobalt from a cobalt-cemented tungsten carbide substrate, liquefies and infiltrates into interstitial regions between the diamond particles. The cobalt acts as a catalyst to promote intergrowth between the diamond particles, which results in formation of a PCD table of bonded diamond grains having diamond-to-diamond bonding therebetween that is bonded to the cemented tungsten carbide substrate. Interstitial regions between the bonded diamond grains are occupied by the metal-solvent catalyst. Once formed, the PCD table may be leached so as to remove at least a portion of the cobalt or other metal-solvent catalyst.

Characteristics of the unsintered diamond particles used in the manufacturing process can affect the properties of the resulting PCD table and PDC. In addition, with existing processes, it can be difficult to determine whether any given characteristic of the diamond particles being used in the process falls within acceptable limits. As such, certain characteristics of the diamond particles may not be known, which can result in inefficiencies.

SUMMARY

Embodiments of the invention relate to methods of measuring at least one rheological property of diamond particles used in the manufacture of PCD, such as a PCD table of a PDC. The inventor has found that certain rheological properties (e.g., torsional mechanical properties or other flow properties) of diamond particles may correlate to a distribution of different sized particles within a diamond particle mixture. For example, the fraction of "fine" versus larger diamond particles within the diamond particle mixture greatly influences such torsional mechanical properties. As such, by measuring a rheological property of the diamond particle mixture, it may be determined whether the diamond particle mixture includes an appropriate fraction of large and fine particles. In other words, the measured rheological property correlates to a degree of deviation (if any) from a target specification of the distribution of diamond particle sizes of the diamond particle mixture.

In an embodiment, a method of measuring at least one rheological property of diamond particles used in the manufacture of polycrystalline diamond is disclosed. The method includes providing diamond particles including a plurality of unsintered diamond particles, measuring the at least one rheological property of the diamond particles, and determining whether the diamond particles are within an acceptable range of a target specification for the at least one rheological property. In a further embodiment, if the diamond particles are within the acceptable range of the target specification, a PDC may be fabricated in an HPHT process in which a PCD table thereof is manufactured using the diamond particles.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

DETAILED DESCRIPTION

Embodiments of the invention relate to methods of a measuring at least one rheological property of diamond particles used in the manufacture of a PCD table and fabricating PDCs using the diamond particles. For example, the diamond particles measured may exhibit a single mode, or a bi-modal or greater particle size distribution. Certain rheological properties of the diamond particles (e.g., torsional mechanical properties or other flow properties) may correlate with agglomeration of a portion of the diamond particles, higher amount of fine diamond particles, lower amount of fine diamond particles, absence of all fines diamond particles below a specified diamond particle size, other characteristics, or combinations of the foregoing. A rheological property of the diamond particles may correlate to a degree of deviation (if any) from a target specification (e.g., diamond particle size distribution) of the diamond particles measured. By comparing the measured value of the at least one rheological property to that of a baseline known to correlate to the desired target specification, it may be determined whether the diamond particles are within an acceptable range relative to the target specification. Such a method may be incorporated into methods for manufacturing a PCD table and/or a PDC so as to ensure the characteristic(s) of the diamond particles used to form the PCD table.

The disclosed methods enable measuring at least one rheological property of diamond particles before the PCD table and/or PDC is formed. Without such measurement, certain characteristics of the diamond particles may not become apparent until after the PCD tables and/or PDCs have been formed, which can result in significant wasted diamond materials and loss of labor when the PCD tables and/or PDCs are non-conforming. By checking, for example, the particle size distribution of the diamond particles prior to HPHT processing, the resulting PCD table may be improved. This determination may be accomplished without directly measuring the particle size distribution of the diamond particles (which can be slow and costly), but by measuring a torsional mechanical property that correlates to the particle size distribution. Such measurement may be accomplished more quickly and less expensively than direct measurement of the particle distribution.

Figure 1A:
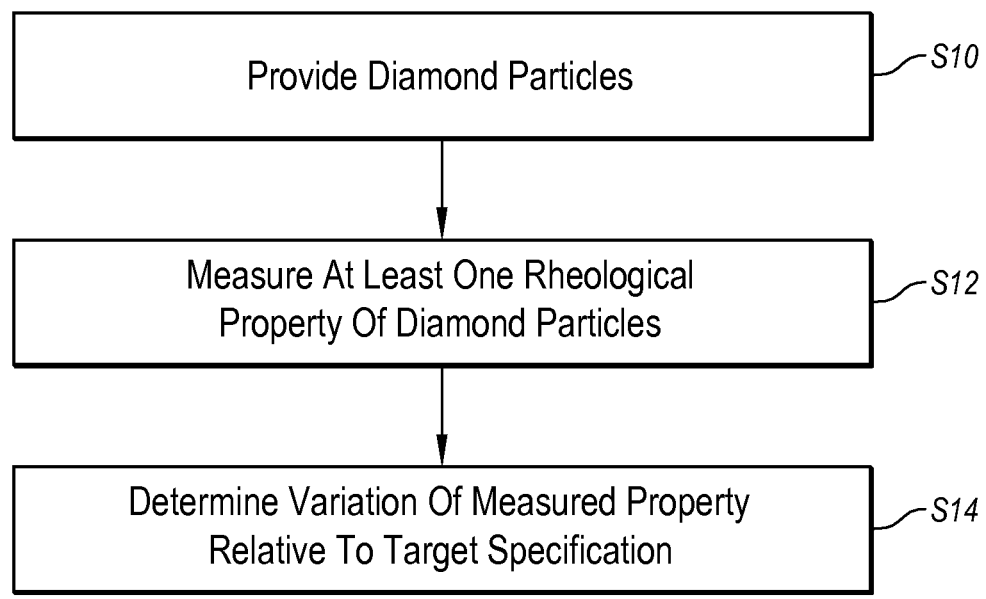
FIG. 1A is a flow chart illustrating an embodiment of a method of measuring at least one rheological property of diamond particles used in the manufacture of a PCD table.
Figure 1B:
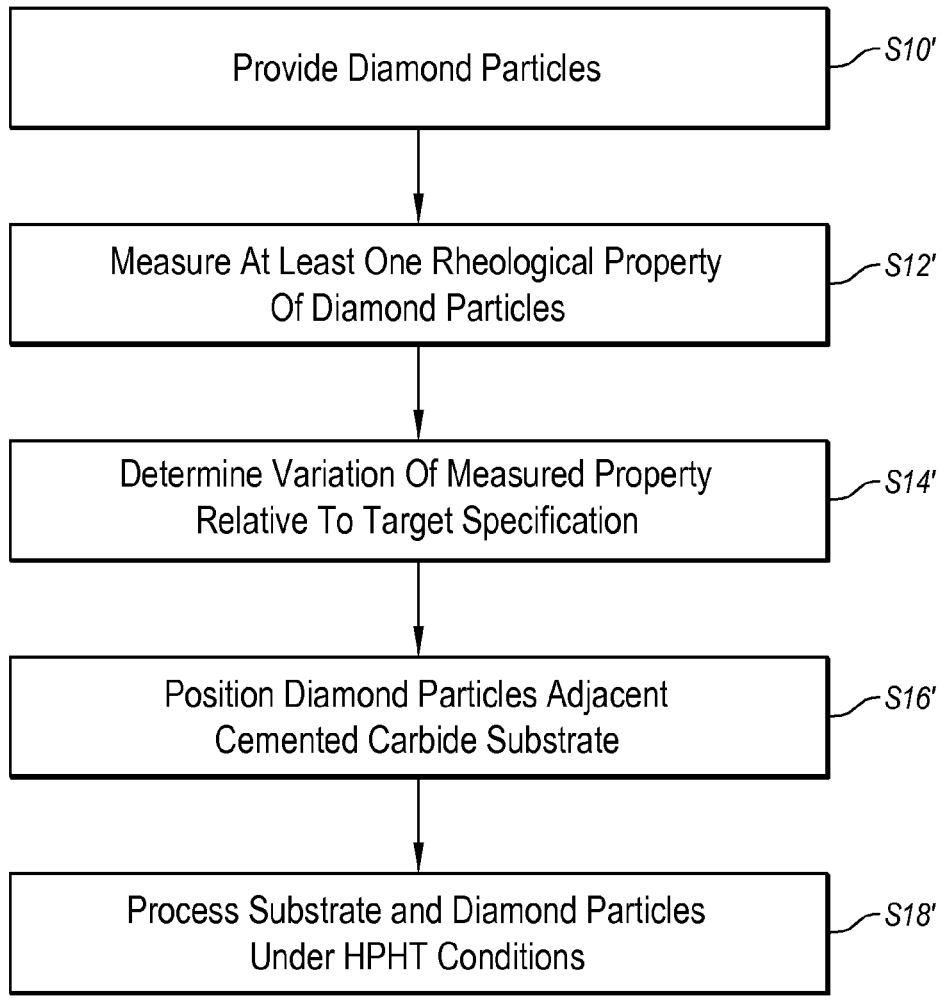
FIG. 1B is a flow chart illustrating a detailed embodiment of a method of manufacturing a PCD table in which at least one rheological property of the employed diamond particles is measured prior to the PCD table being formed.

FIG. 1A is a flow chart illustrating an embodiment of a method of at least one rheological property of diamond particles used in the manufacture of a PCD table. FIG. 1B is a flow chart illustrating a more detailed embodiment of a method for manufacturing a PCD table that incorporates the method of FIG. 1A. As shown in FIG. 1A, at S10 diamond particles are provided, at S12 a rheological property of the diamond particles and/or other flow property is measured, and at S14 any variation of the measured rheological property relative to a target specification is determined.

In the more detailed flow chart of FIG. 1B, at S10' diamond particles are provided, and at S12' a rheological property (e.g., unconfined failure strength as a function of consolidating stress) of the diamond particles and/or other flow property is measured, at S14' any variation between the target specification of the measured property and the actual measured property of the diamond particles is determined. For example, the diamond particles provided at S10' may form a diamond particle mixture prepared from two or more average diamond particles sizes. In the case where the measured value of the rheological property is outside of an acceptable range, the diamond particles may be rejected, reformulated, or otherwise used in a different application, rather than continuing on to S16'. At S16' (assuming the measured value is within an acceptable range relative to the target specification), the diamond particles are positioned adjacent a cemented carbide substrate, and at S18' the substrate and diamond particles are processed under HPHT conditions to form a PDC. Such processing promotes intergrowth between diamond particles, which results in formation of a PCD table of bonded diamond grains having diamond-to-diamond bonding (e.g., sp$^3$ bonding) therebetween.

Figure 2:
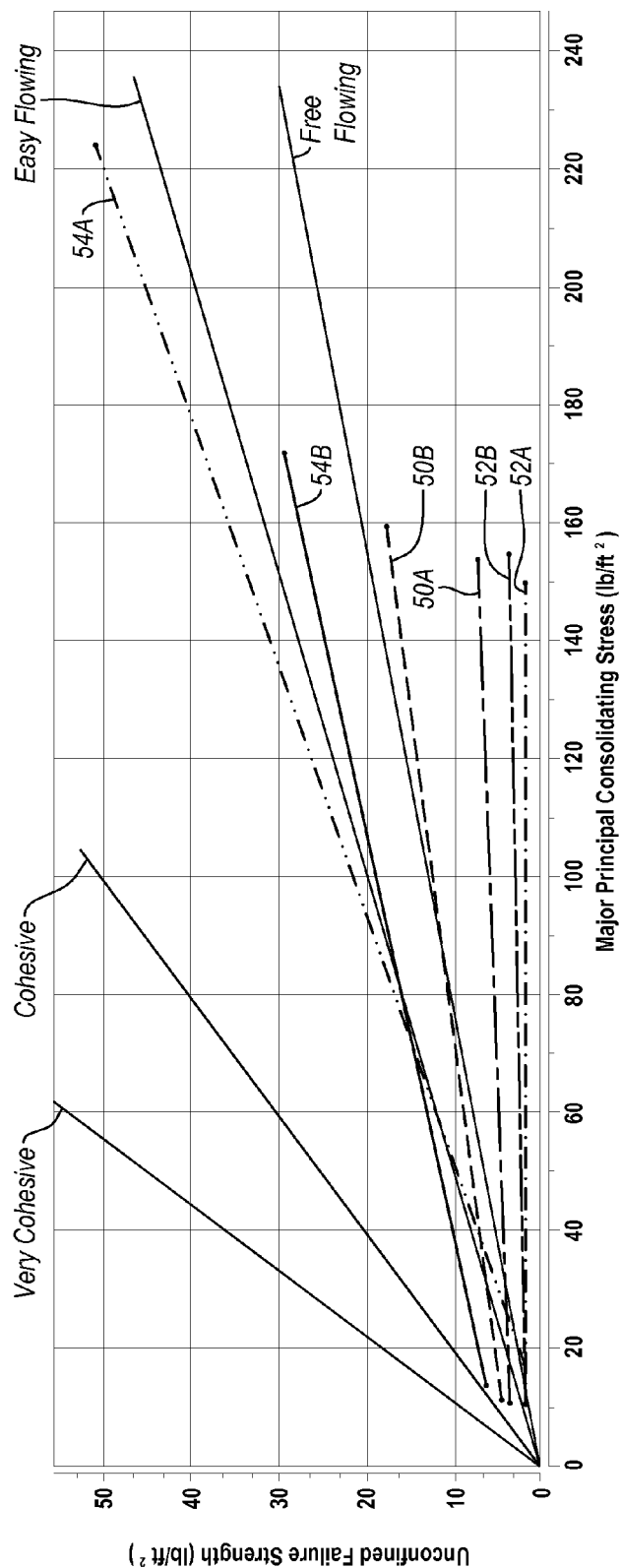
FIG. 2 is a graph illustrating measured rheological properties of various tested diamond particle mixtures.

FIG. 2 is a graph illustrating the measured rheological properties of several example diamond particle mixtures, which can be measured at S12 and S12' shown in the methods of FIGS. 1A and 1B. As shown in the graph, unconfined failure strength (kPa) is plotted as a function of major principal consolidating stress (kPa). Different regions of the graph correspond to the ease with which a powder composition will flow. For example, flow characteristics may be characterized as "very cohesive," "cohesive," "easy flowing," or "free flowing." At any given consolidating stress, more easily flowing powder compositions will exhibit a lower unconfined failure strength. The inventors have found that the formulation of the diamond particle mixture (i.e., the distribution and/or weight fraction of each average particle size included in the mixture) greatly influences such a measured rheological property. As seen in FIG. 2, baselines 50A, 50B for a diamond particle mixture within specification (i.e., having a desired weight fraction of "fine" diamond particles versus larger diamond particles) were measured. Baselines 50A and 50B represent separate measurements made on the same diamond particle mixture.

Measurements made on diamond particle mixtures having different distributions of diamond particle sizes resulted in large differences in the measured "unconfined failure strength" value. For example, the data points along lines 52A, 52B were taken on a diamond particle mixture that included a smaller fraction of small diamond particles (i.e., fines) and a larger fraction of relatively larger diamond particles. Lines 52A and 52B represent separate measurements made on the same diamond particle mixture. The data points along lines 54A, 54B were taken on a diamond particle mixture that included a larger fraction of small diamond particles (i.e., fines) and a smaller fraction of relatively larger diamond particles. Lines 54A and 54B represent separate measurements made on the same diamond particle mixture.

As seen in FIG. 2, diamond particle mixtures corresponding to lines 54A, 54B are significantly more cohesive and less easily flow than lines 50A, 50B. In addition, diamond particle mixtures corresponding to lines 52A, 52B are even freer flowing than lines 50A, 50B. Although the formulation represented by lines 52A, 52B may be more desirable from a flow characteristics perspective, the presence of too large a concentration of "fines" within the diamond particle mixture may negatively affect the quality and/or properties of the PCD table manufactured therefrom for certain applications. Defects associated with the diamond particle mixtures corresponding to lines 52A, 52B, 54A, and 54B may include agglomeration of a portion of the diamond particles, higher amount of fine diamond particles, lower amount of fine diamond particles, absence of all fines diamond particles below a specified diamond particle size, or combinations of the foregoing. Thus, measurement of the unconfined failure strength may be used to determine if a diamond particle mixture is out of specification and exhibits one or more of the above-mentioned defects.

The unconfined failure strength shown in FIG. 2 is a rheological property of the diamond particles. For example, unconfined failure strength may generally be considered a mechanical property of the diamond particles and, more particularly, a torsional mechanical property of the diamond particles. It may be measured by compressing a sample of the diamond particles, bringing a rotatable spindle in contact with the compressed sample, and measuring the rotational force applied to the spindle as the spindle is rotated through the sample. Such measurements may also be used to determine variation within a given diamond particle mixture batch (i.e., consistency quality), or to determine variation in the measured property as a function of time (i.e., determine shelf-life). Other rheological properties that may be measured in addition to or as an alternative to unconfined failure strength that may correlate to diamond particle size distribution include, but are not limited to, bulk density, cohesive strength, angle of wall friction, and angle of internal friction.

Various models of commercially available rheological apparatuses capable of measuring such rheological properties of the diamond particles are available from Freeman Technology Ltd. (e.g., model FT4), and Brookfield Engineering Laboratories, Inc. (e.g., model PFT). Freeman Technology Ltd is located in Great Neck, N.Y., and Brookfield Engineering Laboratories, Inc. is located in Middleboro, Mass.

Figure 3A:
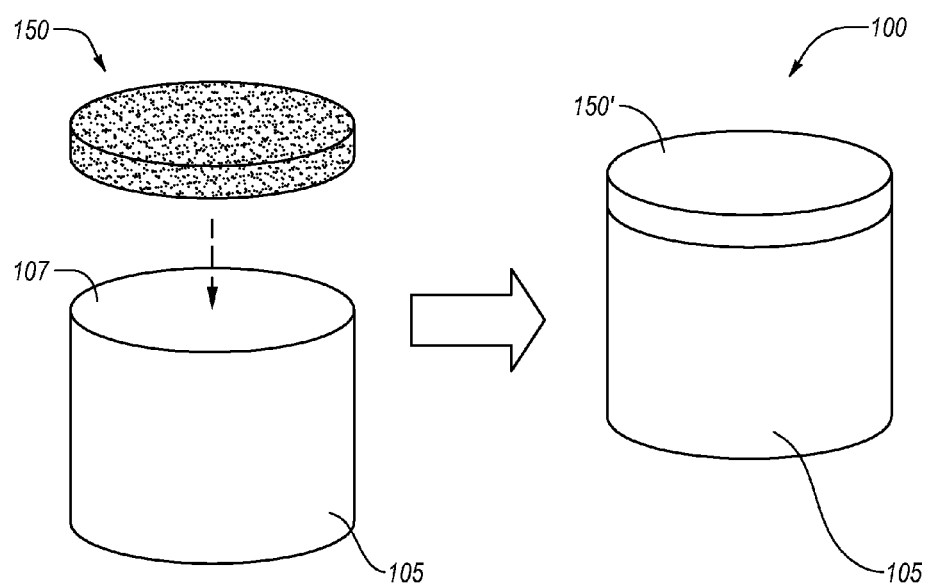
FIG. 3A is a schematic illustrating an embodiment of a method of manufacturing a PDC including a PCD table and a cemented carbide substrate.
Figure 3B:
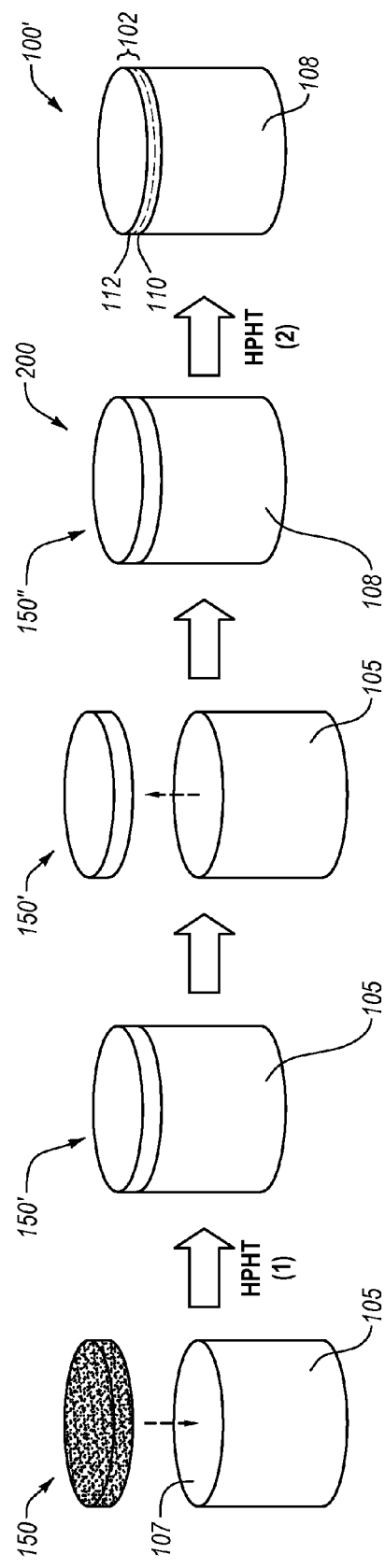
FIG. 3B is a schematic illustrating an embodiment of another method of manufacturing a PDC including a PCD table and a cemented carbide substrate.

FIGS. 3A and 3B are schematic illustrations of embodiments of methods of fabricating a PDC (e.g., shown in FIG. 4) using diamond particles that have been measured in accordance with the methods disclosed herein. The diamond particle size distribution of the diamond particles may exhibit a single mode, or may be a bi-modal or greater particle size distribution. In an embodiment, the diamond particles of the one or more layers of diamond particles 150 may comprise a relatively larger size and at least one relatively smaller size. For example, a bi-modal or greater particle size distribution may be formed by mixing diamond particles of a first average particle size with diamond particles of a second average particle size that differs from the first average particle size to form a diamond particle mixture. As used herein, the phrases "relatively larger" and "relatively smaller" refer to particle sizes (by any suitable method) that differ by at least a factor of two (e.g., 30 μm and 15 μm). According to various embodiments, the diamond particles may include a portion exhibiting a relatively larger average particle size (e.g., 70 μm, 50 μm, 40 μm, 30 μm, 20 μm, 15 μm, 12 μm, 10 μm, 8 μm) and another portion exhibiting at least one relatively smaller average particle size (e.g., 6 μm, 5 μm, 4 μm, 3 μm, 2 μm, 1 μm, 0.5 μm, less than 0.5 μm, 0.1 μm, less than 0.1 μm). In an embodiment, the diamond particles may include a portion exhibiting a relatively larger average particle size between about 5 μm and about 40 μm (e.g., between about 10 μm and about 40 μm) and another portion exhibiting a relatively smaller average particle size (i.e., "fines") between about 1 μm and about 10 μm (e.g., between about 1 μm and about 4 μm). In some embodiments, the diamond particles may comprise three or more different average particle sizes (e.g., one relatively larger average particle size and two or more relatively smaller average particle sizes), without limitation. Additionally, in some embodiments, a sintering additive chosen from graphite, fullerenes, ultra-dispersed diamond particles, or combinations thereof may be mixed with the diamond particles. The sintering additive provides additional carbon apart from the diamond in the form of $sp^2$ carbon that is ultimately fully or partially converted to diamond during HPHT processing. For example, the additive may be present in the diamond particles mixture in an amount of about 1 wt % to about 10 wt %, such as 3 wt % to about 6 wt % or 5 wt %.

The "fines" may comprise between 0 and about 50 percent by weight of the diamond particle mixture, such as about 2 to about 20 percent by weight, about 5 percent by weight, about 10 percent by weight, about 15 percent by weight, about 20 percent by weight, about 25 percent by weight, about 30 percent by weight, about 35 percent by weight, about 40 percent by weight, about 45 percent by weight, or about 50 percent by weight. In a diamond particle mixture including only two average particle sizes (i.e., bi-modal), the balance of the diamond particle mixture may comprise diamond particles having a larger average particle size (e.g., about 10 μm to about 40 μm). In embodiments including three or more average particle sizes, the diamond particles of any given average particle size may comprise between greater than 0 and about 50 percent by weight of the diamond particle mixture. In such embodiments, the actual weight fraction may be any of those values disclosed above within the range of greater than 0 to about 50 weight percent.

It is noted that the as-sintered diamond grain size may differ from the average particle size of the diamond particles prior to sintering due to a variety of different physical processes, such as grain growth, diamond particles fracturing, carbon provided from another carbon source (e.g., dissolved carbon in the metal-solvent catalyst), or combinations of the foregoing.

The cemented carbide substrate 105 and the one or more layers of diamond particles 150 may be placed in a pressure transmitting medium, such as a refractory metal can embedded in pyrophyllite or other pressure transmitting medium. The pressure transmitting medium, including the cemented carbide substrate 105 and the one or more layers of diamond particles 150 therein, may be subjected to an HPHT process using an ultra-high pressure press to create temperature and pressure conditions at which diamond is stable. The temperature of the HPHT process may be at least about 1000° C. (e.g., about 1200° C. to about 1600° C.) and the pressure of the HPHT process may be at least 4.0 GPa (e.g., about 5.0 GPa to about 12.0 GPa) for a time sufficient to sinter the diamond particles to form a PCD table 150'. For example, the pressure of the HPHT process may be about 5 GPa to about 7 GPa and the temperature of the HPHT process may be about 1150° C. to about 1450° C. (e.g., about 1200° C. to about 1400° C.).

During the HPHT process, the metal-solvent catalyst cementing constituent from the cemented carbide substrate 105 (e.g., cobalt from a cobalt-cemented tungsten carbide substrate) may be liquefied and may infiltrate into the diamond particles of the one or more layers of diamond particles 150. The infiltrated metal-solvent catalyst cementing constituent functions as a catalyst that catalyzes initial formation of directly bonded-together diamond grains to form PDC 100 including the PCD table 150' attached to the cemented carbide substrate 105.

In other embodiments, instead of using the cemented carbide substrate 105 to provide the metal-solvent catalyst during sintering of the diamond particles, metal-solvent-catalyst particles (e.g., cobalt powder) may be mixed with the diamond particles and/or a metal-solvent-catalyst disk (e.g., a cobalt disc) may be placed between to the diamond particles and the cemented carbide substrate 105.

In some embodiments, the metal-solvent catalyst may be at least partially removed from the PCD table 150' by immersing the PCD table 150' in an acid, such as aqua regia, nitric acid, hydrofluoric acid, mixtures thereof, or other suitable acid, to form a porous at least partially leached PCD table that allows fluid to flow therethrough (e.g., from one side to another side). For example, the PCD table 150' may be immersed in the acid for about 2 to about 7 days (e.g., about 3, 5, or 7 days) or for a few weeks (e.g., about 4-6 weeks) depending on the process employed. In some embodiments, a residual amount of the metal-solvent catalyst used to catalyze formation of the diamond-to-diamond bonds of the PCD table 150' may still remain even after leaching. For example, the residual metal-solvent catalyst in the interstitial regions may be about 0.5% to about 2% by weight, such as about 0.8% to about 1.2% by weight.

In embodiments in which the metal-solvent catalyst is provided from the cemented carbide substrate 105, it is noted that because the metal-solvent catalyst is infiltrated into the diamond particle mixture from the cemented carbide substrate 105 including tungsten carbide or other carbide grains cemented with a metal-solvent catalyst (e.g., cobalt, nickel, iron, or alloys thereof), the infiltrated metal-solvent catalyst may carry tungsten therewith, tungsten carbide therewith, another metal therewith, another metal carbide therewith, or combinations of the foregoing. In such embodiments, the PCD table 150' and the at least partially leached PCD table may include such material(s) disposed interstitially between the bonded diamond grains. The tungsten therewith, tungsten carbide therewith, another metal therewith, another metal carbide therewith, or combinations of the foregoing may be at least partially removed by the selected leaching process or may be relatively unaffected by the selected leaching process.

Alternatively, the PCD table may be formed by a two-step process in which the diamond particles are sintered so as to form a PCD table, which is then removed from the cemented carbide substrate, and then subsequently re-attached to another cemented carbide substrate. FIG. 3B is a schematic illustration of an embodiment of such a method for fabricating a PDC. The plurality of diamond particles of the one or more layers of diamond particles 150 may be positioned adjacent to an interfacial surface 107 of a first cemented carbide substrate 105.

Just as the embodiment illustrated in FIG. 3A, the diamond particle size distribution of the diamond particles may exhibit a single mode, or may be a bi-modal or greater particle size distribution. For example, a bi-modal or greater particle size distribution may be formed by mixing diamond particles of a first average particle size with diamond particles of a second average particle size that differs from the first average particle size to form a diamond particle mixture. The diamond particles may include a portion exhibiting a relatively larger average particle size (e.g., 70 µm, 50 µm, 40 µm, 30 µm, 20 µm, 15 µm, 12 µm, 10 µm, 8 µm) and another portion exhibiting at least one relatively smaller average particle size (e.g., 6 µm, 5 µm, 4 µm, 3 µm, 2 µm, 1 µm, 0.5 µm, less than 0.5 µm, 0.1 µm, less than 0.1 µm). In an embodiment, the diamond particles may include a portion exhibiting a relatively larger average particle size between about 10 µm and about 40 µm and another portion exhibiting a relatively smaller average particle size between about 1 µm and about 10 µm (i.e., "fines"). In some embodiments, the diamond particles may comprise three or more different average particle sizes (e.g., one relatively larger average particle size and two or more relatively smaller average particle sizes), without limitation.

The "fines" may comprise between 0 and about 50 percent by weight of the diamond particles, such as about 2 to about 20 percent by weight, about 5 percent by weight, about 10 percent by weight, about 15 percent by weight, about 20 percent by weight, about 25 percent by weight, about 30 percent by weight, about 35 percent by weight, about 40 percent by weight, about 45 percent by weight, or about 50 percent by weight. When the diamond particles including only two average particle sizes, the balance of the diamond particles may comprise diamond particles having a larger average particle size (e.g., about 10 µm to about 40 µm). In embodiments including three or more average particle sizes, the diamond particles of any given average particle size may comprise between 0 and about 50 percent by weight of the diamond particle mixture. In such embodiments, the actual weight fraction may be any of those values defined above within the range of 0 to about 50 weight percent.

The first cemented carbide substrate 105 and the one or more layers of diamond particles 150 may be placed in a pressure transmitting medium, such as a refractory metal can embedded in pyrophyllite or other pressure transmitting medium. The pressure transmitting medium, including the first cemented carbide substrate 105 and the one or more layers of diamond particles 150 therein, may be subjected to a first HPHT process using an ultra-high pressure press to create temperature and pressure conditions at which diamond is stable. The temperature of the first HPHT process may be at least about 1000° C. (e.g., about 1200° C. to about 1600° C.) and the pressure of the first HPHT process may be at least 4.0 GPa (e.g., about 5.0 GPa to about 12.0 GPa) for a time sufficient to sinter the diamond particles to form the PCD table 150'. For example, the pressure of the first HPHT process may be about 5 GPa to about 7 GPa and the temperature of the first HPHT process may be about 1150° C. to about 1450° C. (e.g., about 1200° C. to about 1400° C.).

During the first HPHT process, the metal-solvent catalyst cementing constituent from the first cemented carbide substrate 105 may be liquefied and may infiltrate into the diamond particles of the one or more layers of diamond particles 150. The infiltrated metal-solvent catalyst cementing constituent functions as a catalyst that catalyzes initial formation of directly bonded-together diamond grains to form the PCD table 150'.

In an alternative to using the first cemented carbide substrate 105 during sintering of the diamond particles, the PCD table 150' may be formed by placing the diamond particles along with a metal-solvent catalyst (e.g., cobalt powder and/or a cobalt disc) in a pressure transmitting medium, such as a refractory metal can embedded in pyrophyllite or other pressure transmitting medium. The pressure transmitting medium, including the diamond particles and metal-solvent catalyst therein, may be subjected to a first HPHT process using an ultra-high pressure press to create temperature and pressure conditions at which diamond is stable. Such a process will result in the formation of a PCD table 150' separate from any cemented carbide substrate 105.

In embodiments in which the PCD table 150' is formed so as to be metallurgically bonded to a cemented carbide substrate, the PCD table 150' may then be separated from the first cemented carbide substrate 105, as shown in FIG. 3B. For example, the PCD table 150' may be separated from the first cemented carbide substrate 105 by grinding and/or lapping away the first cemented carbide substrate 105, electro-discharge machining, or combinations of the foregoing material removal processes.

Whether the first cemented carbide substrate 105 is employed during formation of the PCD table 150' or not, the metal-solvent catalyst may be at least partially removed from the PCD table 150' by immersing the PCD table 150' in an acid, such as aqua regia, nitric acid, hydrofluoric acid, mixtures thereof, or other suitable acid, to form a porous at least partially leached PCD table 150" that allows fluid to flow therethrough (e.g., from one side to another side). For example, the PCD table 150' may be immersed in the acid for about 2 to about 7 days (e.g., about 3, 5, or 7 days) or for a few weeks (e.g., about 4-6 weeks) depending on the process employed. In some embodiments, a residual amount of the metal-solvent catalyst used to catalyze formation of the diamond-to-diamond bonds of the PCD table 150' may still remain even after leaching. For example, the residual metal-solvent catalyst in the interstitial regions may be about 0.5% to about 2% by weight, such as about 0.8% to about 1.2% by weight.

As shown in FIG. 3B, the PCD table 150" is placed with a cemented carbide substrate 108 to which the PCD table 150" is to be attached to form an assembly 200. The assembly 200 may be placed in a pressure transmitting medium, such as a refractory metal can embedded in pyrophyllite or other pressure transmitting medium. The pressure transmitting medium, including the assembly 200, may be subjected to a second HPHT process using an ultra-high pressure press to create temperature and pressure conditions at which diamond is stable. The temperature of the second HPHT process may be at least about 1000° C. (e.g., about 1200° C. to about 1600° C.) and the pressure of the second HPHT process may be at least 4.0 GPa (e.g., about 5.0 GPa to about 12.0 GPa) so that the infiltrant (e.g., the metallic cementing constituent) in the cemented carbide substrate 108 is liquefied and infiltrates into the PCD table 150". Upon cooling from the second HPHT process, the partially infiltrated PCD table 102 is metallurgically bonded to the cemented carbide substrate 108.

As an alternative to using the cemented carbide substrate 108 as an infiltrant source, an infiltrant layer (e.g., a cobalt disc) may be disposed between the cemented carbide substrate 108 and the PCD table 150". In such an embodiment, the infiltrant layer may liquefy and infiltrate into the PCD table 150" during the second HPHT process.

The depth of penetration of the infiltrant may depend on the pressure, temperature, and process time of the second HPHT process. In some embodiments, the infiltrant may penetrate through substantially the entire depth of the PCD table 102. In some embodiments, the infiltrant may be leached from the PCD table 102 to a selected depth from an upper an/or a side working surface. In other embodiments, infiltrant penetration may be limited so that the infiltrant occupies the interstitial regions of a first region 110 adjacent the second cemented carbide substrate 108, while a second region 112 adjacent the top of the PCD table 102 is not infiltrated. Infiltrant that occupies the interstitial regions of the PCD table 102 may be at least partially removed in a subsequent leaching process using an acid, such as aqua regia, nitric acid, hydrofluoric acid, mixtures thereof, or other suitable acid. Even in embodiments where infiltration is not complete (i.e., a second region 112 that is substantially free of infiltrant is present), it may still be desirable to leach second region 112 so as to improve the uniformity of the interface between the first region 110 and the second region 112, which may improve thermal stability and/or wear resistance in the finished PDC 100'.

PDCs and PCD tables formed according to the inventive methods in which at least one characteristic of the diamond particles is measured prior to sintering may exhibit lower variability and/or non-conformity rates as compared to other processes in which the characteristics of the diamond particles are not verified prior to sintering. The use of the described process, in which a torsional mechanical property of the unsintered diamond particles is measured, enables verification that the specifications for the diamond particles are met. This may result in decreased variability and/or waste of both materials and labor, and can be easily and quickly accomplished, so as to not otherwise significantly slow down the manufacturing process.

Figure 4:
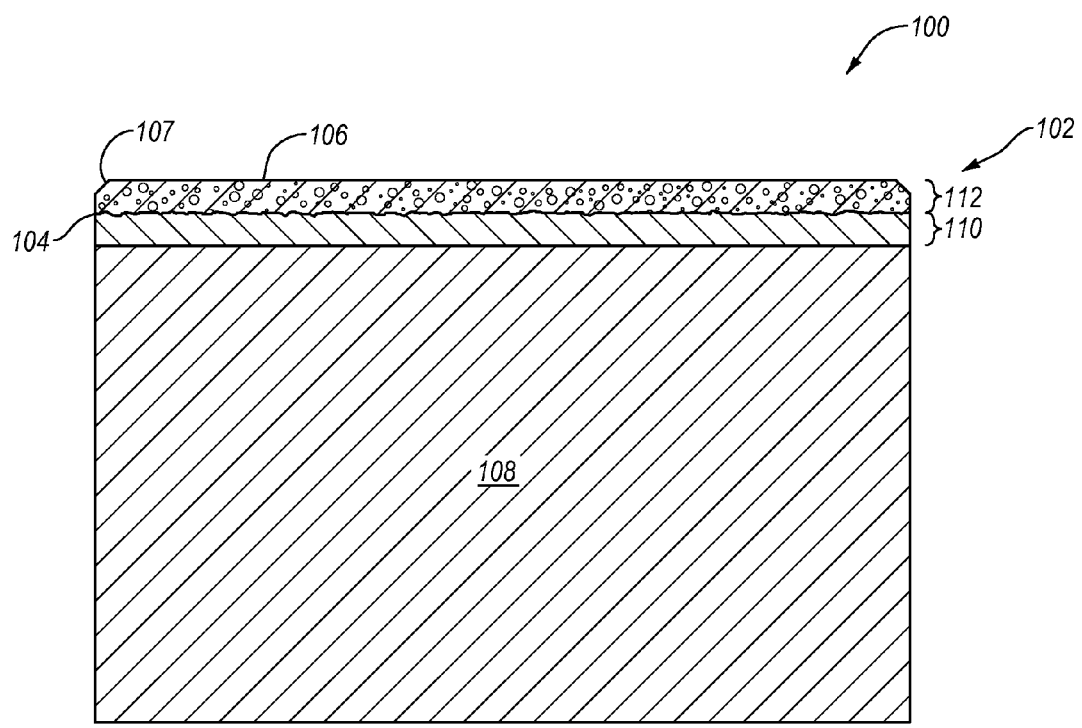
FIG. 4 is a cross-sectional view of the PDC shown in FIG. 3B.

FIG. 4 is a cross-sectional view of an embodiment of the PDC 100 shown in FIG. 3B. The PCD table 102 may be at least partially leached (e.g., with a suitable acid) so as to remove some or all of the metal-solvent catalyst or infiltrant residing within the interstitial regions.

The PCD table 102 includes a plurality of directly bonded-together diamond grains exhibiting diamond-to-diamond bonding (e.g., $sp^3$ bonding) therebetween, which define a plurality of interstitial regions. The PCD table 102 includes at least one lateral surface 104 and an upper exterior surface 106. It is noted that at least a portion of the at least one lateral surface 104 and/or the upper exterior surface 106 may function as a cutting surface that contacts a subterranean formation during drilling operations. In some embodiments, a chamfer 107 may extend between the lateral surface 104 and working surface 106.

In an embodiment, the substrate 108 comprises a plurality of tungsten carbide or other carbide grains (e.g., tantalum carbide, vanadium carbide, niobium carbide, chromium carbide, and/or titanium carbide) cemented together with a metallic cementing constituent, such as cobalt, iron, nickel, or alloys thereof. For example, in an embodiment, the substrate 108 may be a cobalt-cemented tungsten carbide substrate. In some embodiments, the substrate 108 may include two or more different carbides (e.g., tungsten carbide and titanium carbide).

Figure 5:
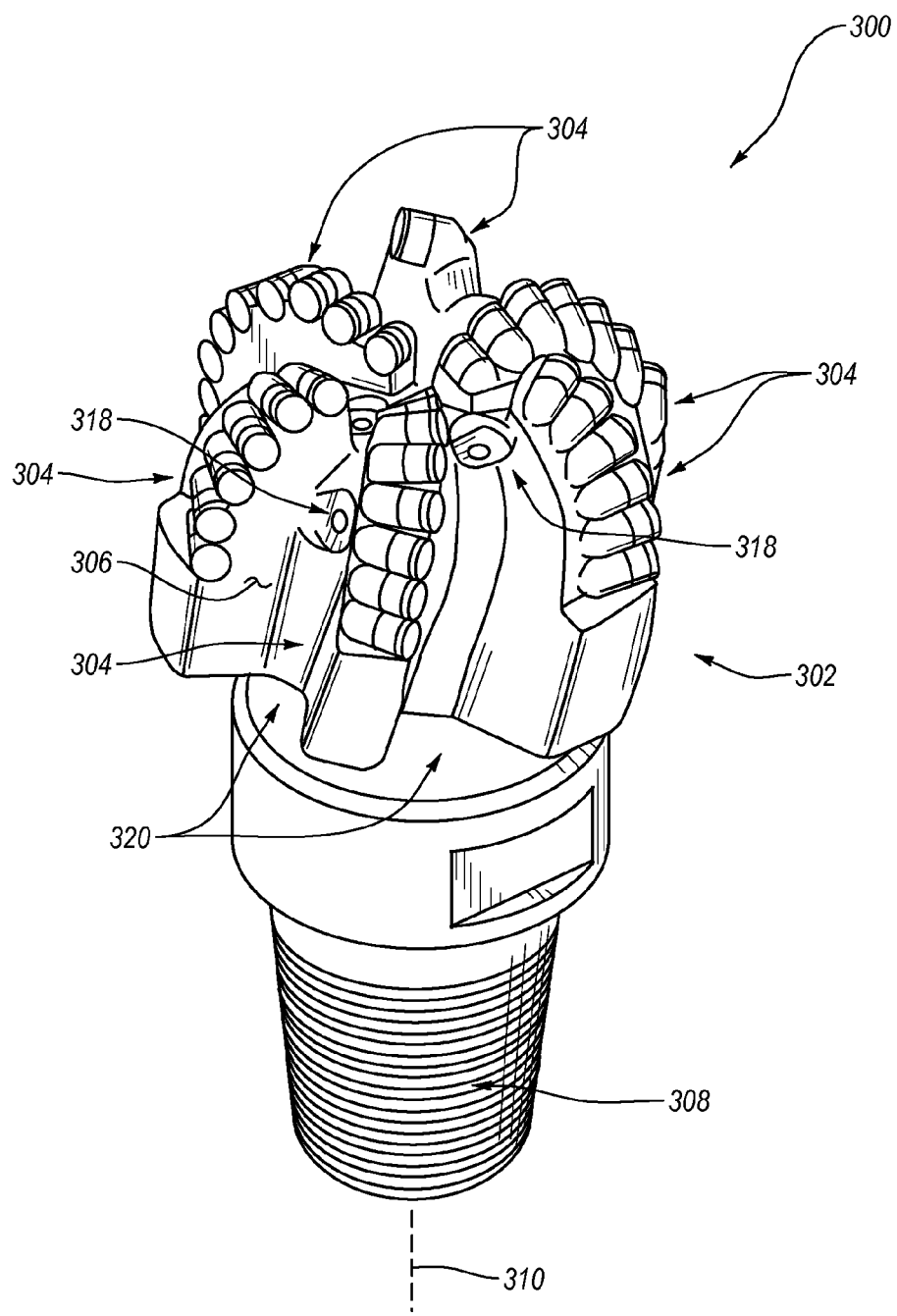
FIG. 5 is an isometric view of an embodiment of a rotary drill bit that may employ one or more of the PDCs manufactured according to one or more embodiments of the invention.
Figure 6:
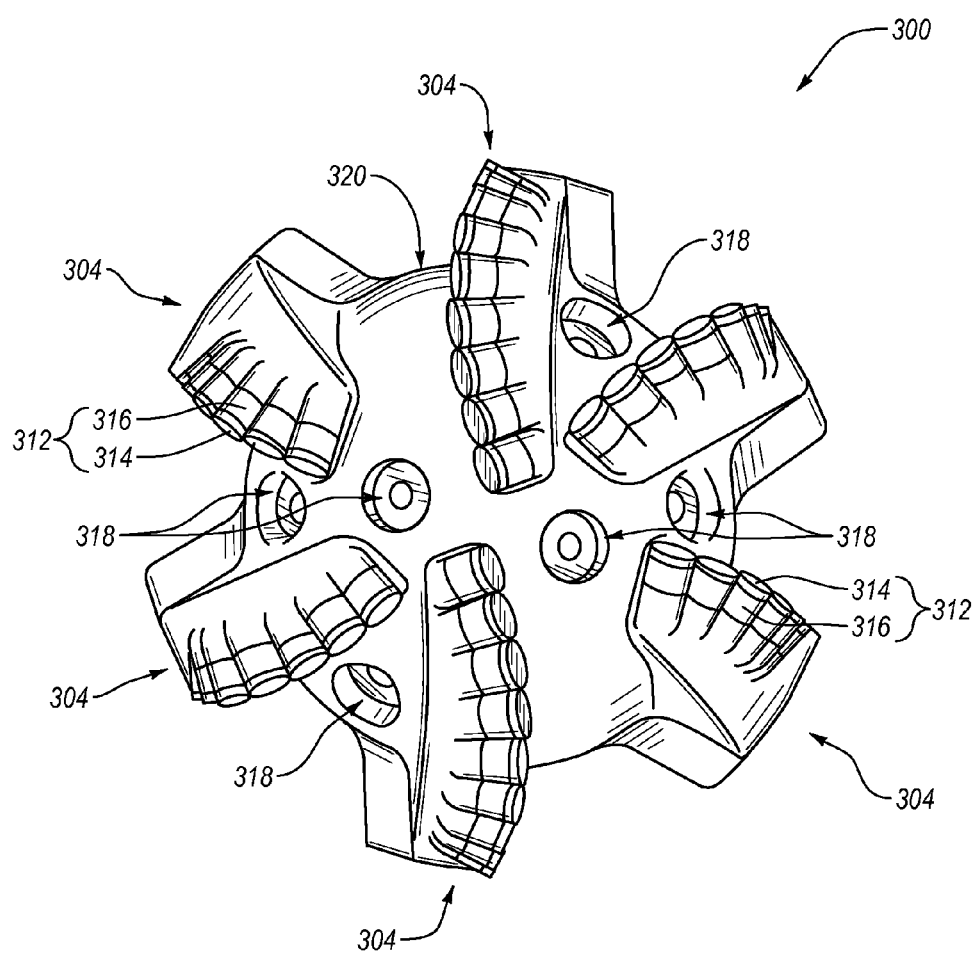
FIG. 6 is a top elevation view of the rotary drill bit shown in FIG. 5.

The PCD elements and PDCs manufactured according to the inventive method may be installed on a rotary drill bit. FIG. 5 is an isometric view and FIG. 6 is a top elevation view of an embodiment of a rotary drill bit 300 that includes at least one PDC manufactured according to any of the disclosed PDC embodiments. The rotary drill bit 300 comprises a bit body 302 that includes radially and longitudinally extending blades 304 having leading faces 306, and a threaded pin connection 308 for connecting the bit body 302 to a drilling string. The bit body 302 defines a leading end structure for drilling into a subterranean formation by rotation about a longitudinal axis 310 and application of weight-on-bit. At least one PDC, manufactured according to any of the previously described embodiments, may be affixed to the bit body 302. With reference to FIG. 6, each of a plurality of PDCs 312 is secured to the blades 304 of the bit body 302 (FIG. 5). For example, each PDC 312 may include a PCD table 314 bonded to a substrate 316. More generally, the PDCs 312 may comprise any PDC disclosed herein, without limitation, which is manufactured according to any of the previously described embodiments. Circumferentially adjacent blades 304 define so-called junk slots 320 therebetween. Additionally, the rotary drill bit 300 includes a plurality of nozzle cavities 318 for communicating drilling fluid from the interior of the rotary drill bit 300 to the PDCs 312.

FIGS. 5 and 6 merely depict one embodiment of a rotary drill bit that employs at least one PDC tested and structured in accordance with the disclosed embodiments, without limitation. The rotary drill bit 300 is used to represent any number of earth-boring tools or drilling tools, including, for example, core bits, roller-cone bits, fixed-cutter bits, eccentric bits, bi-center bits, reamers, reamer wings, or any other downhole tool including superabrasive compacts, without limitation.

The PDCs manufactured from diamond particles measured in accordance with the methods disclosed herein (e.g., PDC 100 of FIG. 4) may also be utilized in applications other than cutting technology. For example, the disclosed PDC embodiments may be used in wire dies, bearings, artificial joints, inserts, cutting elements, and heat sinks Thus, any of the PDCs disclosed herein may be employed in an article of manufacture including at least one superabrasive element or compact.

Thus, the PDCs disclosed herein may be used in any apparatus or structure in which at least one conventional PDC is typically used. In one embodiment, a rotor and a stator, assembled to form a thrust-bearing apparatus, may each include one or more PDCs (e.g., PDC 100 of FIG. 4) configured according to any of the embodiments disclosed herein and may be operably assembled to a downhole drilling assembly. U.S. Pat. Nos. 4,410,054; 4,560,014; 5,364,192; 5,368,398; and 5,480,233, the disclosure of each of which is incorporated herein, in its entirety, by this reference, disclose subterranean drilling systems within which bearing apparatuses utilizing superabrasive compacts disclosed herein may be incorporated. The embodiments of PDCs disclosed herein may also form all or part of heat sinks, wire dies, bearing elements, cutting elements, cutting inserts (e.g., on a roller-cone-type drill bit), machining inserts, or any other article of manufacture as known in the art. Other examples of articles of manufacture that may use any of the PDCs disclosed herein are disclosed in U.S. Pat. Nos. 4,811,801; 4,268,276; 4,468,138; 4,738,322; 4,913,247; 5,016,718; 5,092,687; 5,120,327; 5,135,061; 5,154,245; 5,460,233; 5,544,713; and 6,793,681, the disclosure of each of which is incorporated herein, in its entirety, by this reference.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, are open ended and shall have the same meaning as the word "comprising" and variants thereof (e.g., "comprise" and "comprises").

What is claimed is:

1. A method of measuring at least one rheological property of diamond particles used in the manufacture of polycrystalline diamond, the method comprising:
   providing a mixture batch of diamond particles including a plurality of unsintered diamond particles exhibiting agglomerates;
   measuring the at least one rheological property of the mixture batch of diamond particles exhibiting the agglomerates;
   correlating the at least one rheological property of the mixture batch of diamond particles with agglomeration of a portion of the plurality of unsintered diamond particles and amount of the plurality of unsintered diamond particles below a selected particle size;
   determining whether the at least one rheological property of the mixture batch of diamond particles is within an acceptable range of a target specification for the at least one rheological property;
   repeating the measuring, correlating and determining acts on the mixture batch of unsintered diamond particles over a period of time; and
   determining a variation in the at least one rheological property over the period of time to determine agglomeration as a function of time and thereby determine an acceptable shelf-life of the mixture batch.

2. The method as recited in claim 1 wherein the target specification comprises a distribution of diamond particles.

3. The method as recited in claim 1 wherein the measured at least one rheological property comprises a torsional mechanical property.

4. The method as recited in claim 1 wherein the measured at least rheological property comprises unconfined failure strength as a function of consolidating stress.

5. The method as recited in claim 1 wherein determining whether the at least one rheological property of the mixture batch of diamond particles exhibiting the agglomerates is within an acceptable range of a target specification for the at least one rheological property comprises determining whether the mixture batch of diamond particles exhibiting the agglomerates exhibit a diamond particle size distribution that falls within the acceptable range of the target specification.

6. The method as recited in claim 1 wherein determining whether the at least one rheological property of the mixture batch of diamond particles exhibiting the agglomerates is within an acceptable range of a target specification for the at least one rheological property comprises determining whether the mixture batch of diamond particles exhibiting the agglomerates exhibit an amount of agglomeration that falls within the acceptable range of the target specification.

7. The method as recited in claim 1 wherein determining whether the at least one rheological property of the mixture batch of diamond particles exhibiting the agglomerates is within an acceptable range of a target specification for the at least one rheological property comprises determining whether the mixture batch of diamond particles exhibiting the agglomerates exhibit an amount of diamond particles below a selected particle size.

8. The method as recited in claim 1 wherein determining whether the at least one rheological property of the mixture batch of diamond particles exhibiting the agglomerates is within an acceptable range of a target specification for the at least one rheological property comprises determining whether the mixture batch of diamond particles exhibiting the agglomerates exhibit an amount of diamond particles above a selected particle size.

9. The method as recited in claim 1 wherein providing the mixture batch of diamond particles including a plurality of unsintered diamond particles exhibiting the agglomerates comprises mixing diamond particles having at least two average particle sizes.

10. The method as recited in claim 9 wherein mixing diamond particles having at least two average particle sizes comprises mixing diamond particles having an average particle size between about 5 µm and about 40 µm with diamond particles having an average particle size between about 1 µm and about 15 µm.

11. The method as recited in claim 10 wherein the mixture batch of diamond particles comprise between about 2 percent by weight and about 20 percent by weight of diamond particles having the smaller of the average particle sizes.

12. The method as recited in claim 1, further comprising accepting or rejecting the diamond particles at least partially based on the act of determining whether the at least one rheological property of the mixture batch of diamond particles exhibiting agglomeration is within an acceptable range of a target specification for the at least one rheological property.

13. A method of measuring at least one rheological property of diamond particles used in the manufacture of polycrystalline diamond, the method comprising:
   forming a diamond particle mixture including mixing diamond particles having an average particle size between about 5 µm and about 40 µm with diamond particles having an average particle size between about 1 µm and about 15 µm, wherein between about 2 percent by weight and about 20 percent by weight of diamond particles exhibit the smaller of the average particle sizes;
   measuring the at least one rheological property of the diamond particle mixture that correlates to a distribution of the diamond particles of the diamond particle mixture;
   determining whether the correlated distribution of diamond particles is within an acceptable range of a target specification; and
   if the correlated distribution is outside of the acceptable range of the target specification, reformulating the diamond particle mixture to fall within the acceptable range of the target specification.

14. The method as recited in claim 13 wherein the at least one rheological property comprises a torsional mechanical property.

15. The method as recited in claim 13 wherein the at least one rheological property comprises unconfined failure strength as a function of consolidating stress.

16. The method as recited in claim 13 wherein determining whether the diamond particle mixture is within an acceptable range of the target specification comprises determining whether the diamond particle mixture exhibits a diamond particle size distribution that falls within the acceptable range of the target specification.

17. The method as recited in claim 13 wherein determining whether the diamond particle mixture is within an acceptable range of the target specification comprises determining whether the diamond particle mixture exhibits an amount of agglomeration that falls within the acceptable range of the target specification.

18. The method as recited in claim 13 wherein determining whether the diamond particle mixture is within an acceptable range of the target specification comprises determining whether the diamond particle mixture exhibits an amount of diamond particles below a selected particle size.

19. The method as recited in claim 13 wherein determining whether the diamond particle mixture is within an acceptable range of the target specification comprises determining whether the diamond particle mixture exhibits an amount of diamond particles above a selected particle size.

20. A method of measuring at least one rheological property of diamond particles used in the manufacture of polycrystalline diamond, the method comprising:
   providing a mixture batch of diamond particles including a plurality of unsintered diamond particles by mixing a first portion of unsintered diamond particles having an particle size between about 5 µm and about 40 µm with a second portion of unsintered diamond particles having an average particle size between about 1 µm and about 15 µm;
   measuring the at least one rheological property of the mixture batch of diamond particles;
   correlating the at least one rheological property of the mixture batch of diamond particles with agglomeration of a portion of the plurality of unsintered diamond particles and amount of the plurality of unsintered diamond particles below a selected particle size; and
   determining whether the at least one rheological property of the mixture batch of diamond particles is within an acceptable range of a target specification for the at least one rheological property.

\* \* \* \* \*